(12) United States Patent
Rasansky

(10) Patent No.: US 11,574,346 B2
(45) Date of Patent: Feb. 7, 2023

(54) CONTEXT-BASED FEEDBACK SYSTEM AND METHOD

(71) Applicant: CLX Health LLC, Newark, DE (US)

(72) Inventor: Richard A. Rasansky, Narberth, PA (US)

(73) Assignee: CLX HEALTH LLC, Newark, DE (US)

(*) Notice: Subject to any disclaimer, the term of this patent is extended or adjusted under 35 U.S.C. 154(b) by 0 days.

(21) Appl. No.: 17/694,918

(22) Filed: Mar. 15, 2022

(65) Prior Publication Data

US 2022/0198535 A1 Jun. 23, 2022

Related U.S. Application Data

(60) Continuation of application No. 16/810,990, filed on Mar. 6, 2020, now abandoned, which is a division of
(Continued)

(51) Int. Cl.
*G06Q 30/02* (2012.01)
*G06Q 50/10* (2012.01)

(52) U.S. Cl.
CPC ......... *G06Q 30/0282* (2013.01); *G06Q 30/02* (2013.01); *G06Q 50/10* (2013.01)

(58) Field of Classification Search
CPC .................. G06Q 30/0282; G06Q 30/02
See application file for complete search history.

(56) References Cited

U.S. PATENT DOCUMENTS 5,537,618 A 7/1996 Boulton et al.
8,601,095 B1 12/2013 Carlson et al.
(Continued)

FOREIGN PATENT DOCUMENTS

KR 1020100081871 7/2010

OTHER PUBLICATIONS

Michael Parent, An Empirical Investigation of Facilitated GSS Support for Marketing Strategy Development by Information-Enabled Alliances, May 1997 (Year: 1997).*
(Continued)

*Primary Examiner* — Maria C Santos-Diaz
(74) *Attorney, Agent, or Firm* — Blank Rome LLP

(57) ABSTRACT

A computer-implemented interactive system, methods, and platform are herein disclosed to allow for the aggregation of context based feedback data according to a selected feedback context model. In an illustrative implementation, the computer-implemented interactive system/platform comprises an exemplary server computer environment, an instruction set comprising one or more instructions to request from the one or more other computing environments feedback data (e.g., such requests being made on a temporal basis according to one or more feedback context models), and a data store. The platform may be used to aggregate feedback data for various feedback sponsors/requestors, by way of example, as a user/customer is experiencing a product/service, in real time. The frequency, timing, and trigger for feedback data requests from users, illustratively, can be tailored by the one or more instructions of the one or more feedback context models that take into account a baseline use/experience of given product/service.

11 Claims, 13 Drawing Sheets

Related U.S. Application Data application No. 15/111,599, filed as application No. PCT/US2015/011386 on Jan. 14, 2015, now abandoned.

(60) Provisional application No. 61/927,303, filed on Jan. 14, 2014.

(56) References Cited

U.S. PATENT DOCUMENTS

| | | |
|---|---|---|
| 9,928,272 B1 | 3/2018 | Niyogi |
| 2011/0264550 A1 | 10/2011 | Fair |
| 2013/0132824 A1 | 5/2013 | Dalal et al. |
| 2013/0268357 A1 | 10/2013 | Heath |
| 2014/0122369 A1 | 5/2014 | Chow |
| 2014/0156460 A1 | 6/2014 | Fan et al. |
| 2015/0227949 A1 | 8/2015 | Sangani |

OTHER PUBLICATIONS

International Search Report dated Apr. 24, 2015; International Application No. PCT/US2015/011386; International Filing Date: Jan. 14, 2015; 3 pages.
Written Opinion dated Apr. 24, 2015; International Application No. PCT/US2015/011386; International Filing Date Jan. 14, 2015; 6 pages.
English translation; Korean Publication No. 1020100081871; Publication Date: Nov. 16, 2010; 17 pages.

\* cited by examiner

CONTEXT-BASED FEEDBACK SYSTEM AND METHOD

CROSS REFERENCE TO RELATED APPLICATIONS

This application is a continuation of U.S. application Ser. No. 16/810,990, filed Mar. 6, 2020; which application is a division of U.S. application Ser. No. 15/111,599, filed Jul. 14, 2016; which application is a U.S. National Stage Application of International Application Serial No. PCT/US2015/011386, filed Jan. 14, 2015; which application claims benefit of priority of U.S. Provisional Application No. 61/927,303, filed Jan. 14, 2014. All of the above-identified related applications are incorporated herein by reference.

FIELD OF THE INVENTION

The present invention relates to a context-based feedback platform and, more specifically, to a system and method for soliciting context-based feedback from a user of a product or service.

BACKGROUND OF THE INVENTION

There exist various systems and platforms that allow users to provide informed opinions regarding products and services. From the simple, such as online surveys, to rating sections found on popular e-commerce websites, such as Amazon.com and eBay, to social networking opinion websites providing consumer experience journal entries/ratings/opinions on a variety of topics including restaurants, entertainment, product review, professional services, etc., the ability to electronically aggregate, manage, and communicate opinion data as well as the pervasive utility and popularity of electronic opinion data channels has resulted in a muddled, noisy, and often confusing opinion/feedback data sphere. The volume of presently available opinion/feedback data in the data sphere (e.g., websites and mobile apps) generally renders it less meaningful to its reader and, more importantly, its sponsor/requestor.

Typically, current feedback platforms (e.g., stand-alone and/or integrated as part of a larger website/app) operate using survey type questions, rating scales, and/or comment boxes which are presented to and requested from a user generally within a prolonged period of time (e.g., one to seven days) after the user has purchased a product or service. Empirically, it has been shown that the quality of the feedback data decays exponentially with increasing time from the point of purchase/experience of a product/service. As such, with current deployments of feedback platforms, the quality of the data is compromised to the detriment of the reader, and, again, more importantly, the feedback data sponsor/requestor.

Another non-optimal and dilutive feature of current feedback systems is the manner in which collected feedback data is presented. In most instances, outside of a focused market research type study/survey, current feedback platforms aggregate and present feedback data as part of a community based data broadcast in which a feedback data contributor seeks to present his/her feedback as part of a community forum (e.g., Yelp.com), social network (e.g., Facebook.com), and/or open/closed broadcast service (e.g., Twitter). This broadcast context promotes feedback data that has been shown to be of less quality (or genuine) given principles of community dynamics (e.g., need to be considered important, contrary, etc.). Furthermore, current platforms request users to enter "reviews" of products and/or services which have been shown to contain a higher level of false information and negative feedback.

Additionally, current feedback platforms do not provide effective presentation and navigation of aggregated feedback data for the benefit of feedback data sponsors/requestors.

From the foregoing, it is appreciated that there exists a need for systems and methods that are aimed to ameliorate the shortcomings of existing feedback platforms.

SUMMARY OF THE INVENTION

A computer-implemented interactive system, method, and platform are herein disclosed to allow for context-based communication of feedback data by users to a feedback sponsor/requestor according to a selected temporal/location/demographic trigger based feedback data collection/aggregation model (feedback context model). In an illustrative implementation, the computer-implemented interactive system/platform comprises an exemplary server computing environment illustratively operable to receive and transmit data from one or more other computer environments, an instruction set comprising one or more instructions to request from the one or more other computing environments feedback data (e.g., such requests being made on a temporal basis according to one or more feedback context models), and a data store operable to store, in real time, aggregated feedback data, and/or one or more feedback data reporting templates. In an example embodiment, the disclosed system, methods, and platform may be used to aggregate feedback data for various feedback sponsors/requestors, by way of example, as a user/customer is experiencing a product/service, in real time. The frequency, timing, and trigger for feedback data requests from users, illustratively, can be tailored by the one or more instructions of the one or more feedback context models that take into account a baseline use/experience of given product/service.

In an illustrative operation, the exemplary server computing environment executes one or more instructions comprising one or more requests from the one or more other computing environments feedback data, such requests being made on a temporal basis according to one or more feedback context models. In the illustrative operation, feedback data is operably received by the exemplary server computing environment and is processed according to a selected feedback data reporting template. The processed data may be made available to the feedback sponsor/requester in a tactical dashboard, which comprises the feedback data and personal information linking the feedback data to the user who provided the feedback data, and also in a strategic dashboard, which comprises aggregated, depersonalized feedback data from a plurality of sponsors/requesters. The dashboards are available for subsequent communication to and display on one or more computing environments of the sponsor/requester.

This Summary of the Invention section is provided to introduce a selection of concepts in a simplified form that are further described below in the Detailed Description of the Invention. This Summary of the Invention section is not intended to identify key features or essential features of the claimed subject matter, nor is it intended to be used to limit the scope of the claimed subject matter. Other features of the herein described systems and methods are further described below.

BRIEF DESCRIPTION OF THE DRAWINGS

For the purpose of illustration, there are shown in the drawings certain embodiments of the present invention. In the drawings, like numerals indicate like elements throughout. It should be understood that the invention is not limited to the precise arrangements, dimensions, and instruments shown. In the drawings.

DETAILED DESCRIPTION OF THE INVENTION

Figure 1:
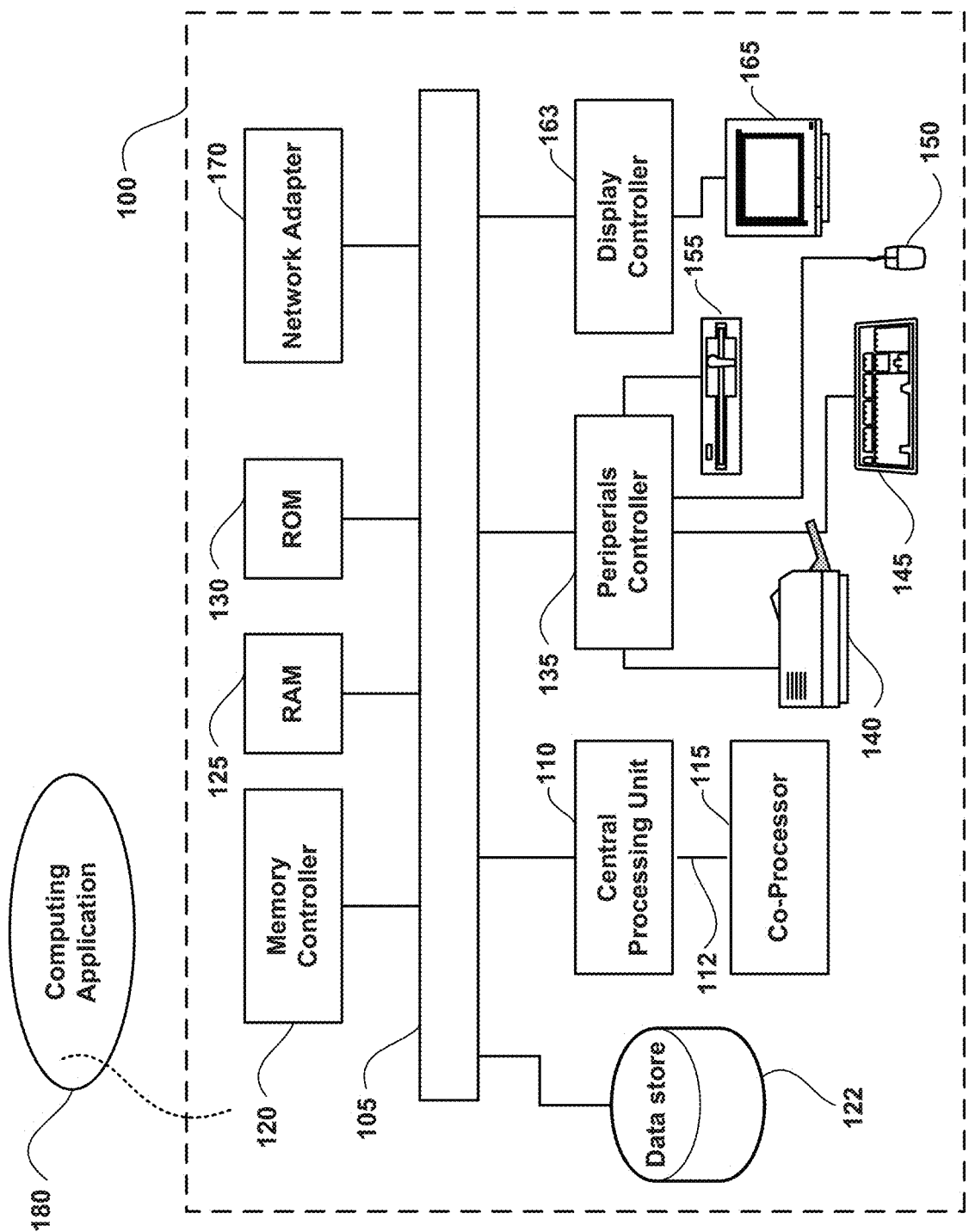
FIG. 1 illustrates a block diagram of an exemplary computing system, in accordance with an exemplary embodiment of the present invention.

Reference to the drawings illustrating various views of exemplary embodiments of the present invention is now made. In the drawings and the description of the drawings herein, certain terminology is used for convenience only and is not to be taken as limiting the embodiments of the present invention. Furthermore, in the drawings and the description below, like numerals indicate like elements throughout.

FIG. 1 depicts an exemplary computing system, generally designated as 100, in accordance with an exemplary embodiment of the present invention. The computing system 100 is capable of executing at least one computing application 180. The computing application 180 can comprise a software application, an applet, a virtual machine that interprets a software script, a browser that renders web pages, or any other software instruction set that may be executed or interpreted by the computing system 100 to perform at least one function, operation, and/or procedure.

In an exemplary embodiment, the computing system 100 is controlled primarily by computer-readable and computer-executable software instructions. The computer-readable and computer-executable software instructions may include instructions for the computing system 100 to store and access the computer-readable and computer-executable software instructions themselves. Such software instructions may be executed within a central processing unit (CPU) 110 of the computing system 100 to cause the computing system 100 to perform the functions described herein. In an exemplary embodiment, the CPU 110 is a microprocessor.

In another exemplary embodiment, the computing system 100 further includes a coprocessor 115, which is an optional processor, distinct from the main CPU 110. The coprocessor 115 performs additional functions or assists the CPU 110. The CPU 110 may be connected to co-processor 115 through an interconnect 112. The coprocessor 115 may be a floating-point coprocessor, also called a numeric or math coprocessor, which is designed to perform numeric calculations faster and better than the general-purpose CPU 110.

In operation, the CPU 110 fetches, decodes, and executes software instructions or, in relevant alternative embodiments, fetches and interprets software scripts. The CPU 110 transfers information to and from other resources via the computing system 110's main data-transfer path, a system bus 105. The system bus 105 connects the components in the computing system 100 and defines the medium for data exchange.

The computing system 100 further includes one or more memory devices, which are coupled to the system bus 105, and a memory controller 120. The memory devices include random access memory (RAM) 125 and read only memory (ROM) 130. Such memories 125, 130 include circuitry that allows information to be stored and retrieved. The ROMs 130 generally contain stored data that cannot be modified. Data stored in the RAM 125 can be read or changed by the CPU 110 or other hardware devices. Access to the RAM 125 and/or ROM 130 may be controlled by the memory controller 120. The memory controller 120 may provide an address translation function that translates virtual addresses into physical addresses as instructions are executed. The computing system 100 further includes a data store 122 for storing data persistently.

The computing system 100 may further include a peripherals controller 135 responsible for communicating instructions from the CPU 110 to peripherals, such as, a printer 140, a keyboard 145, a mouse 150, and a data storage drive 155. The computing system further includes a display 165, a display controller 163 for controlling the display 165, and a network adaptor 170. The display 165 displays visual output generated by the computing system 100. Such visual output may include text, audio, graphics, animated graphics, and video. The display controller 163 includes electronic components required to generate a video signal that is sent to the display 165. The network adaptor 170 may be used to connect the computing system 100 to an external communication network.

The computing system 100 can be deployed as part of a networked computing system comprising a server computing system and one or more client computing systems. In such a networked computing system, the server computing system may be embodied as one or more computing systems 100, and each of the one or more client computing systems may each be embodied as one or more computing systems 100.

Figure 2:
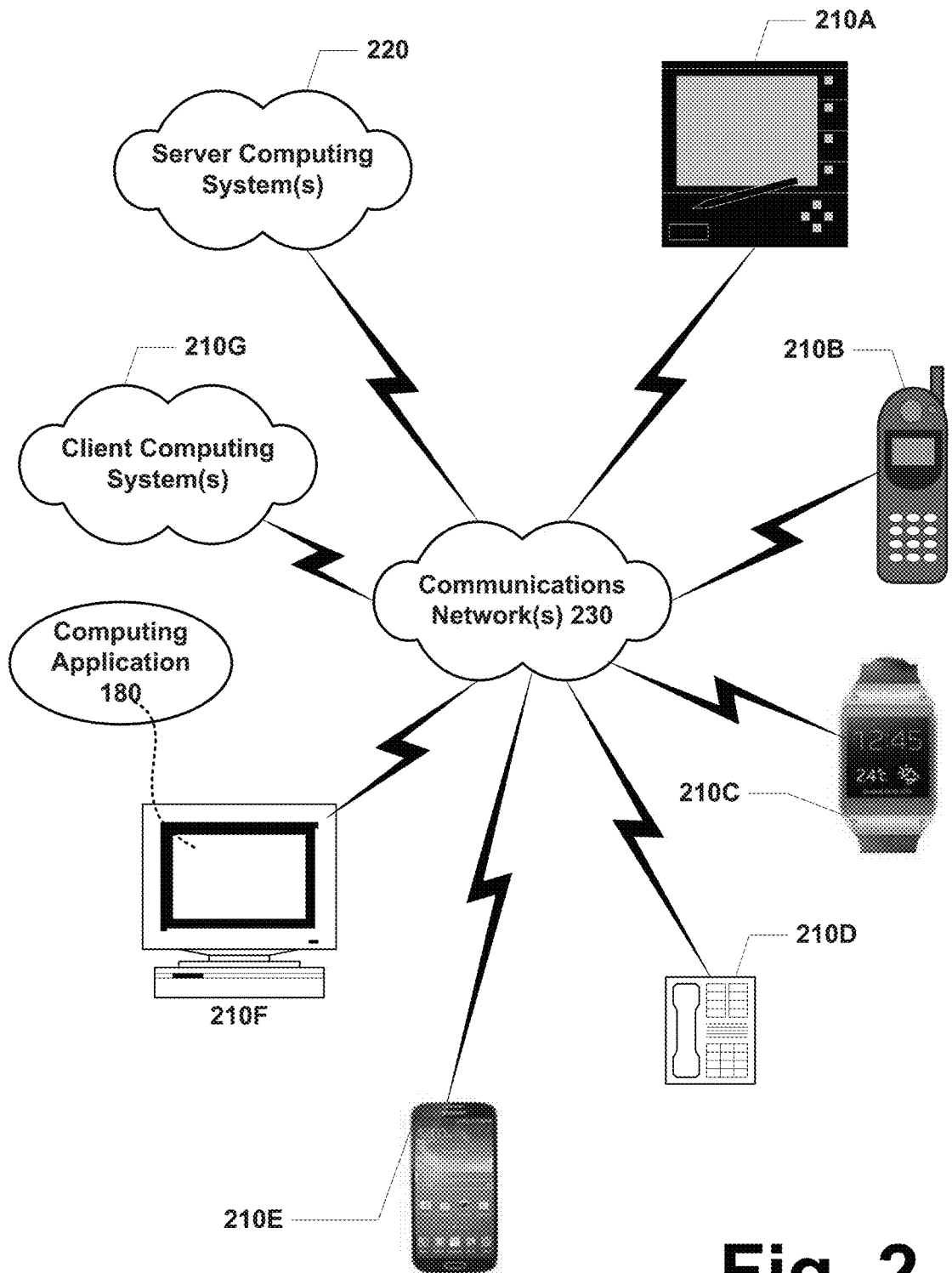
FIG. 2 illustrates a system for providing a context-based feedback platform, in accordance with an exemplary embodiment of the present invention.

Referring now to FIG. 2, there is illustrated an exemplary networked computing system 200, comprising one or more server computing systems 220 in communication with a plurality of client computing systems (referred to hereinafter also as "client computers") 210A through 210G, in accordance with an exemplary embodiment of the present invention. Each of the one or more server computing systems 220 may be embodied as a separate computing system 100. Each of the client computing systems 210A through 210G may be embodied as one or more computing systems 100.

When comprising more than one server computing system 220, the server computing systems 220 form a server cloud for providing services to the one or more client computing systems 210A through 210G. When any of the client computing systems 210A through 210G is embodied as one or more computing systems 100, it forms a cloud for receiving services from the server computing system(s) 220 and providing services to its user. The server computing system(s) 220 may be interconnected via a communications network 230 (which may comprise a combination of a fixed-wire or wireless LAN, WAN, intranet, extranet, peer-to-peer network, virtual private network, the Internet, or other communications networks) with the plurality of client computing systems 210A through 210G.

In a network environment in which the communications network 230 is the Internet, for example, the server computing system(s) 220 may be operable to communicate data to and from the client computing systems 210A through 210G via any of a number of known protocols, such as, hypertext transfer protocol (HTTP), file transfer protocol (FTP), simple object access protocol (SOAP), or wireless application protocol (W AP). Additionally, the networked computing system 200 can utilize various data security protocols such as secured socket layer (SSL), pretty good privacy (PGP), TSL, IPSec to accommodate data security and privacy standards such as HIPAA and/or PCI. Each client computing system 210A through 210G may be equipped with an operating system or other machine instructions operable to support one or more computing applications or communication modalities (e.g., voice, text, e-mail, etc.), such as a web browser, or other graphical user interface, or a mobile desktop environment to gain access to services provided by the server computing system(s) 220.

FIG. 2 illustrates various exemplary embodiments of the client computing systems 210A through 210G. In FIG. 2, the client computing system 210A is tablet personal computer; the client computing system 210B is a mobile telephone; the client computing system 210C is a smartphone watch (and/or personal data tracking device—e.g., FitBit); the client computing system 210D is a telephone; the client computing system 210E is a smart mobile phone (also referred to herein as a "smart phone"); the client computing system 210F is a personal computer; and the client computing system 210G is a cloud computer system comprising any of the foregoing devices. It is to be understood that the client computer systems 210A through 210G are not limited to the embodiments illustrated in FIG. 2 and described herein. Rather, they may comprise any combination of a tablet personal computer, a mobile telephone, a smart phone, a telephone, a personal computer, a smart phone watch, a cloud computer system, or any other computing/data communication device capable of connecting to the Internet either directly or indirectly in combination with another device (e.g., Bluetooth, RFID, NFC). Furthermore it is to be understood that the networked computing system 200 is not limited to the number of client computing system 210A through 210G illustrated in FIG. 2. Rather, any number of client computing systems 210A through 210G is contemplated for use in the system 200.

In operation of the system 200, a user may interact with a computing application 180 running on a computing environment of any of the client computer systems 210A through 210G to input or obtain desired data. The computing application 180 may be stored on a computing environment of the server computer system 220 and made available by the server computer system 220 through the client computer systems 210A through 210G over the communications network 230, e.g., the computing application 180 may be a web application accessed in a web browser, or it may be software downloadable to the client computer systems 210A through 210G and executed independently from a web browser, e.g., the computing application 180 may be an app. In the exemplary embodiment of the client computer system 210D illustrated in FIG. 2, the client computer system 210D is a telephone which is incapable of running a software application 180. Such device provides a user access to voice recognition software running on the server computing system(s) 220 to input or obtain desired data.

A user may request access to specific data and applications housed in whole or in part in a server computing environment provided by the server computing system(s) (server cloud) 220. These data may be communicated between client computing environments running on the client computing systems 210A through 210G and the server computing environment for processing and storage. The server computing environment may host computing applications, processes, scripts, and applets for the generation, authentication, encryption, and communication of data and applications and may cooperate with other server computing environments (not shown), third party service providers (not shown), network attached storage (NAS) and storage area networks (SAN) to realize application/data transactions.

In an exemplary embodiment, the client computing environments access the data and user interface through web browsers running on the client computing systems 210A through 210G. In another exemplary embodiment, the client computing environments access the data and user interface through apps running on the client computing systems 210A through 210G independently of web browsers.

Figure 3:
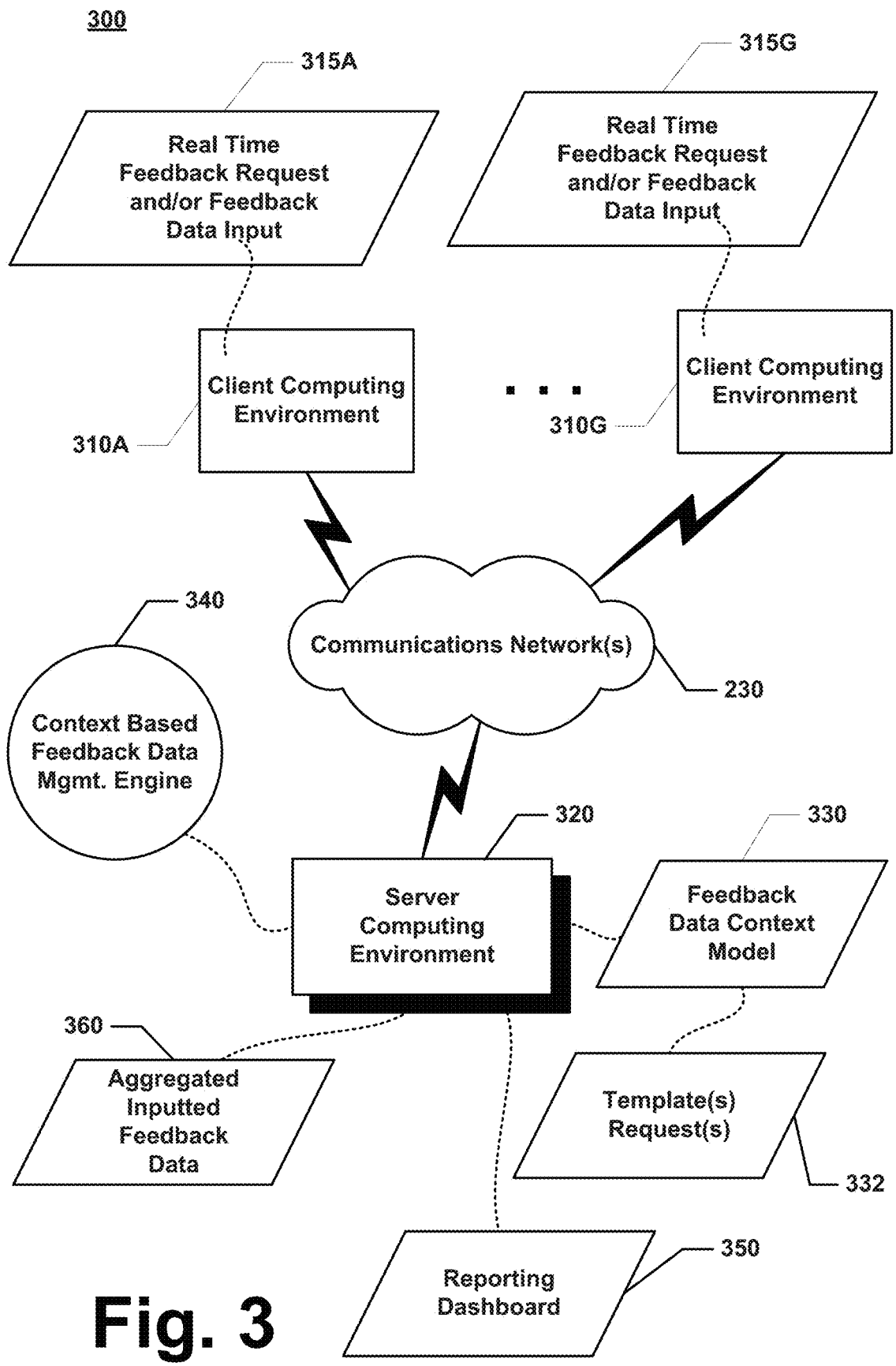
FIG. 3 illustrates a context-based feedback data environment comprising a server computing environment and one or more client computing environments, in accordance with an exemplary embodiment of the present invention.

Referring now to FIG. 3, there is illustrated a feedback data environment, generally designated as 300, in accordance with an exemplary embodiment of the present invention. The feedback data environment 300 comprises a server computing environment 320, the communications network(s) 230, and client computing environments 310A through 310G. The server computing environment 320 is a software environment that is executed on the server computing system(s) 220, and the client computing environments 310A through 310G are software environments that are executed, respectively, on the client computing systems 210A through 210G.

The client computing environments 310A through 310G are operable to receive input from respective users or operators of the client computing systems 210A through 210G and to transmit a portion or all of the input to the server computing environment 320. The client computing environments 310A through 310G are also operable to display information, such as information provided by the server environment 320 in response to the input transmitted to it. The input comprises real time feedback requests and/or feedback data 315A through 315G, received respectively by the client computing environments 310A through 310G from respective users or operators. The information displayed by the client computing environments 310A through 310G may comprise the feedback data 315A through 315G previously inputted.

For discussion purposes below, the client computing environments 310A through 310G are generally referred to as the "client computing environment 310"; the real time feedback requests and/or feedback data 315A through 315G are generally referred to as the "real time feedback requests and/or feedback data 315"; and the client computer systems 210A through 210G are generally referred to as the "client computer system 210" or "client computer 210." It is to be understood that all references to the client computing environment 310 below apply to any of the client computing environments 310A through 310G; that all references to the real time feedback requests and/or feedback data 315 apply to any of the real time feedback requests and/or feedback data 315A through 315G; and that all references to the client computer system 210 apply to any of the client computer systems 210A through 210G.

During operation of the feedback data environment 300, the client computing environment 310 transmits a request 315 to the server computing environment 320 via the communications network(s) 230 to begin a context-based feedback process, in accordance with an exemplary embodiment of the present invention. The server computing environment 320 receives the request 315 and begins executing a context-based feedback data management engine 340 to begin the context-based feedback process.

During execution of the context-based feedback data management engine 340, the server computing environment 320 loads data representative of a feedback data context model selected from one or more feedback data context models 330 stored in the data store 122 based on the request 315. Each feedback data context model 330 specifies an interface comprising one or more requests 332 soliciting feedback from the user or operator of the client computing environment 310. The server computing environment 320 provides access to the interface of the selected context model 330 via the application 180 and transmits the request(s) 332 of the loaded feedback data context model 330 to the client computing environment 310 thereby.

In response to the request(s) 332 in the interface, the user or operator of the computing environment 310 inputs the feedback data 315 using via the client computing environment 310. The client computing environment 310 transmits such data 315 over the communications network(s) 230 to the server computing environment 320, which stores it in the data store 122.

The loaded feedback data context model 330 comprises an exemplary timeline and/or one or more conditions, e.g., receipt of responsive feedback data 315 to a feedback data request 332 or metadata associated with the user or operator, e.g., the user's or operator's current location, the stage of a service currently being rendered to the user or operator, etc. Based on such feedback data 315 responsive to a first feedback data request 332, the timeline and/or one or more conditions of the loaded feedback data context model 330 specifies a further request 332 to be transmitted by the server computing environment 320 to the computing environment 310 to solicit further feedback data 315. In this way, the feedback requests 332 may be transmitted one-by-one to the client computing environment 310 to the client computing environment 310.

The server computing environment 320 receives the feedback data 315 and stores it in the data store 122 as aggregated inputted feedback data 360. The contextualized provision of further requests 332 by the server computing environment 320 and the receipt of feedback data 315 from the client computing environment 310 continues until no further unanswered requests 332 remain in the template of the loaded model 330.

Each exemplary feedback data context model 330 comprises one or more conditions and/or timelines regarding the collection of feedback data 315A through 315G regarding a user's use of a product and/or a user's experience with a provided service. In an illustrative implementation, exemplary services covered by the feedback data context models 330 can include: a user's experience throughout the various steps of a given healthcare service (e.g., admission, consultation, in-office pre-procedure, in-office post-procedure, nursing, recovery, out-of-office post procedure, etc.), restaurant service (e.g., check in, waiting for the table, in-meal service, entertainment portion, etc.), travel service (e.g., luggage handling, check in, in travel service, transportation, etc.), hotel service (e.g., check in, cleanliness of the room, responsiveness of the hotel staff to service requests, etc.), and so on. The conditions and/or timelines in each exemplary feedback data context model 330 provide that they are context based—one feedback request 332 provided by the server computing environment 320 may depend on the data 315 received in response to another feedback request 332 or one feedback request 332 may depend on metadata concerning the user, e.g., the user's location with a facility, stage of receiving a service, etc.

In the illustrative implementation, the context based feedback management engine 340 executing on the server computing environment 320 is operative to process the received inputted feedback data 315 according to the one or more platform aggregation and analysis engines to populate or update a dashboard 350. The server computing environment 320 communicates the populated dashboard 350 or the updates to the dashboard 350 over the communications network(s) 230 to an authorized, requesting client computing environment 310. In an exemplary embodiment, the server computing environment 320 stores the configurations, e.g., views, of the dashboard 350 in the data store 122.

It is to be understood that the client computing environment 310 used by the user providing the feedback data 315 is not be the same as the client computing environment 310 requesting to view the dashboard 350 provided or updated by the server computing environment 320. In fact, it is expected that such users are not the same. The user requesting access to the dashboard 350 in most cases will be associated with the entity that provided the good or service for which the other user, e.g., a customer of the entity, provided the feedback data input 315.

Figure 4:
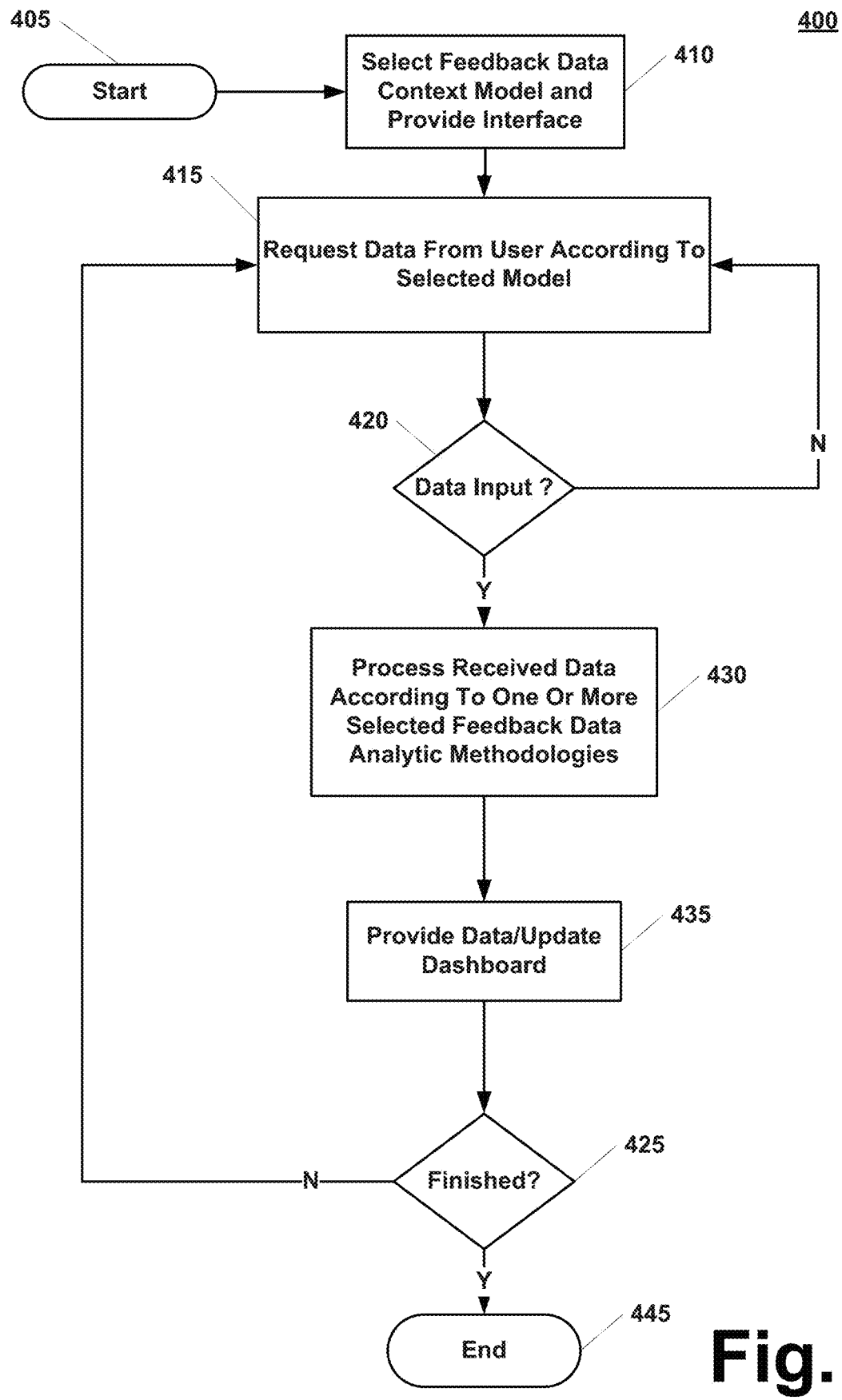
FIG. 4 illustrates a method of providing a context-based feedback service, in accordance with an exemplary embodiment of the present invention.

Referring now to FIG. 4, there is illustrated a method, generally designated as 400, of providing a context-base feedback service, in accordance with an exemplary embodiment of the present invention. FIG. 4 is described with reference to FIG. 3.

The method 400 begins at a Step 405 and proceeds to a Step 410 in which the context based feedback data management engine 340 selects a feedback data context model from the one or more feedback data context models 330 and provides the interface (application 180) of the selected feedback data context model 330 to a client computing environment 310. From there, the method 400 proceeds to a Step 415 in which feedback data 315 is requested from a participating user operating a client computing environment 310 according to the selected one or more feedback data context models 330. Consistent with the description above, the selected feedback data context models 330 may comprise one or more timelines/conditions that trigger the communication of the one or more feedback data requests 332. By way of example, the selected feedback data context model 330 may comprise when data is requested from a participating user as a user uses a given product and/or experiences a particular service.

After the Step 415, the method 400 proceeds to a Step 420 in which a check is performed to determine whether the server computing environment 320 has received feedback data 315 in response to the request 332. If the server computing environment 320 determines that data has not been received, the method 400 reverts to the Step 415 and continues from there. However, if the server computing environment 320 determines in the Step 420 that feedback data has been received responsive to a particular feedback data request 332, the method 400 proceeds to a Step 430.

In the Step 430, the received feedback data 315 is processed according to one or more data analytic methodologies and/or other business logic. From the Step 430, the method 400 proceeds to a Step 435 in which the dashboard 350 is populated (in the instance in which this is the first time that the Step 435 is performed) or updated (in the instance in which this is not the first time that the Step 435 has been performed), and then to a Step 440 in which the dashboard 350 is communicated to the client computing environment 315.

The method 400 proceeds to a Step 440, in which the server computing environment 320 determines whether the method 400 has finished. If it has not, the method 400 reverts to the Step 415. Otherwise, it terminates at a Step 445. Criteria that the server computing environment 320 may use to determine whether the method 400 has finished include whether the user's experience with the product or service has concluded, whether a predetermined amount of time has elapsed, etc.

The steps of the method 400 are performed by the server computing environment 320 operating on the server computing system(s) 220. The steps of the method 400 are embodied in software instructions that are stored in a storage unit, such as the data store 122, of the server computing system(s) 220. The server computing system(s) 220 is configured to access such storage unit to load and execute the software instructions to provide the server computing environment 320 and to perform the steps of the method 400.

Figure 5:
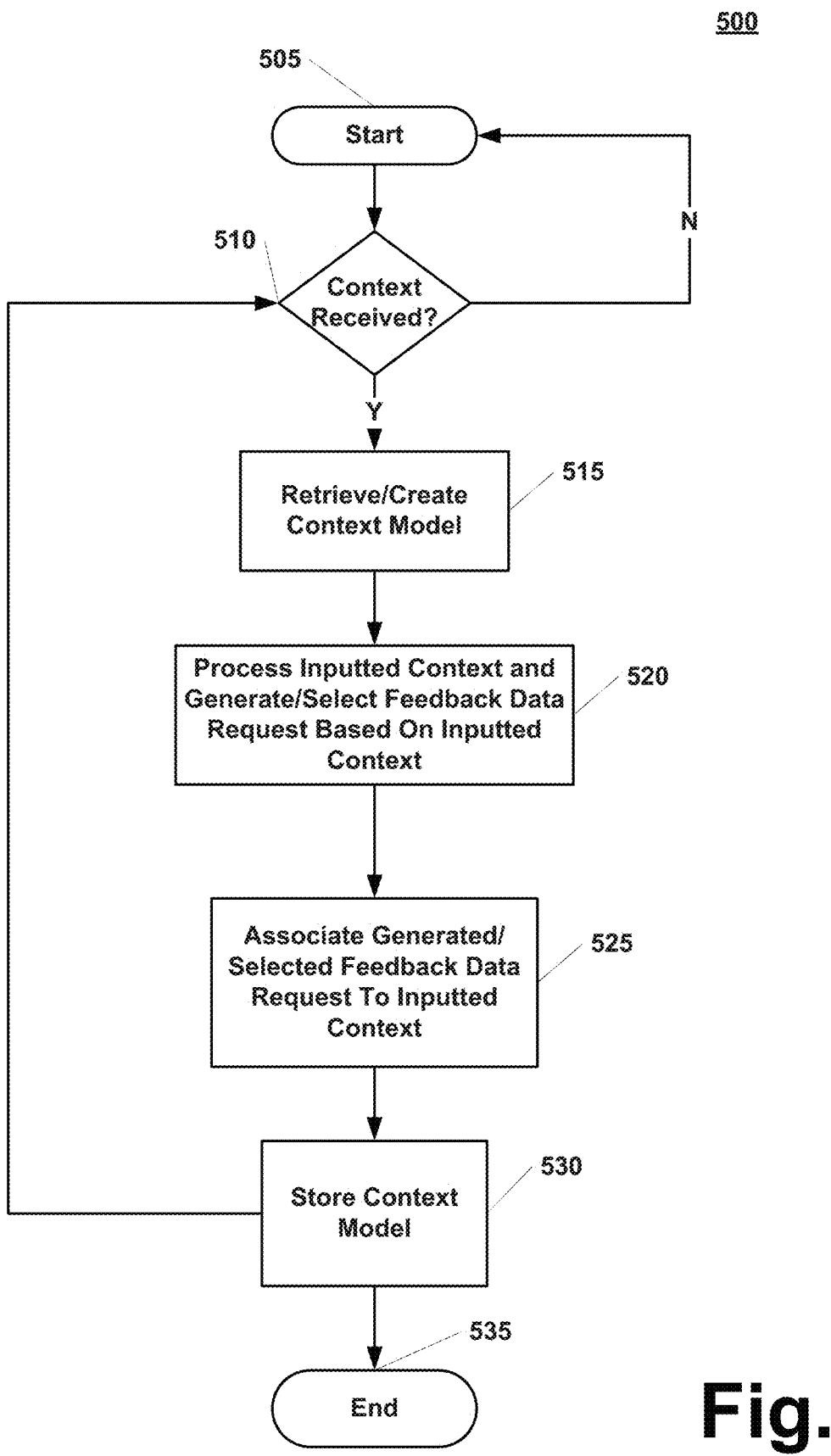
FIG. 5 illustrates a method of defining one or more context-based feedback data models, in accordance with an exemplary embodiment of the present invention.

Referring now to FIG. 5, there is illustrated a method, generally designated as 500, of defining the one or more feedback data context models 330 as part of the operation of the exemplary context feedback data platform 300, in accordance with an exemplary embodiment of the present invention. As is shown, processing begins at a Step 505 and proceeds to a Step 510 in which a check is performed to determine if data representative of a context has been received by the server computing environment 320 from an authorized client computer 310. In an illustrative implementation, a context can comprise the completion of a step in a service offering (e.g., checking in at a hotel) and/or the specific use of a product (e.g., sitting in an automobile). If the check at Step 510 indicates that a context has not been received, processing reverts to the Step 505 and waits for the context input.

However, if the check at the Step 510 indicates that a context has been inputted, processing proceeds to a Step 515 where a feedback data model 330 is created (and/or retrieved from the data store 122 for modification if already created). Processing then proceeds to a Step 520 where the received context is processed to generate one or more feedback data requests 332 based on the inputted context. Processing then proceeds to a Step 525 where the generated feedback data request 332 is associated with the inputted context for subsequent use (e.g., processing of the Step 415 of the method 400). The context model is then stored in a Step 530 in the data store 122 of the server computing system(s) 220. The method 500 then reverts to the Step 510 and continues from there or terminates at a step 535 if the user indicates that there are no further contexts to be inputted.

The steps of the method 500 are performed by the server computing environment 320 operating on the server computing system(s) 220. The steps of the method 500 are embodied in software instructions that are stored in a storage unit, such as the data store 220, of the server 220. The server computing system(s) 220 is configured to access such storage unit to load and execute the software instructions to provide the server computing environment 320 and to perform the steps of the method 500. It is contemplated that the context received by the server computing environment 320 is inputted by a client computing environment 315 that is authorized to request that the server computing environment 320 create a feedback data model 330.

Figure 6B:
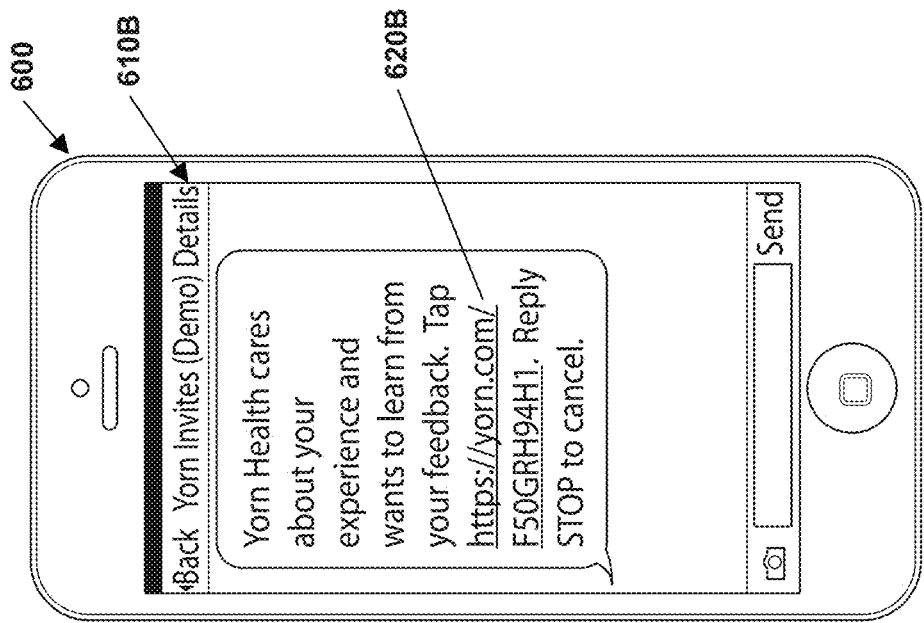
FIGS. 6A-6G illustrate screenshots of an interface by which a user provides feedback, in accordance with an exemplary embodiment of the present invention.
Figure 6A:
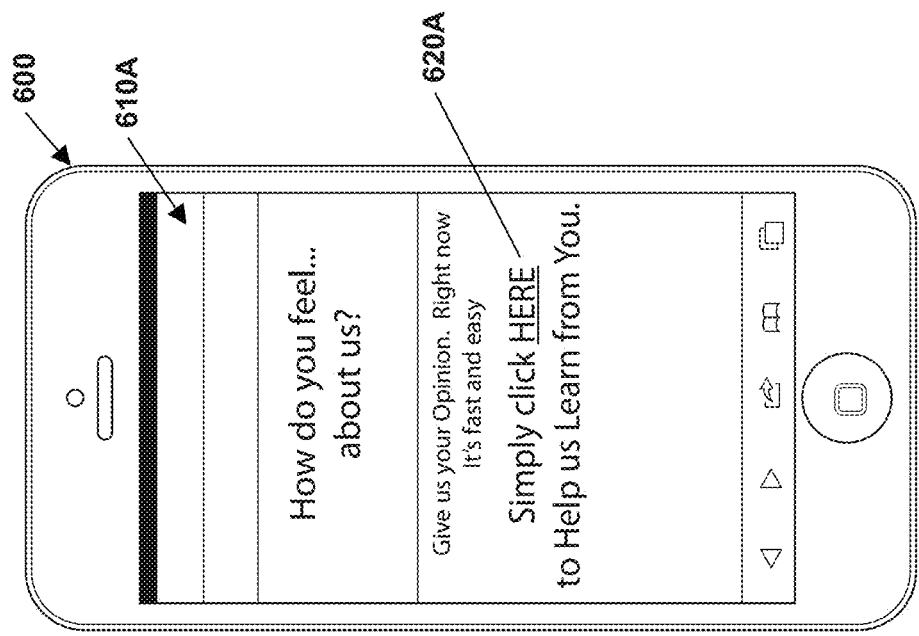

Referring now to FIGS. 6A through 6G, there are illustrated exemplary screen shots of various screens of a smart phone 600, in accordance with an exemplary embodiment of the present invention. FIG. 6A illustrates a first embodiment of an access screen 610A which comprises a link 620A for accessing an interface of a feedback data context model 330. The link 620A is personalized for the user of the smart phone 600. When the user selects the link 620A, the smart phone 600 sends a request 315 to the server computing environment 320 to gain access to the interface of the linked-to feedback data context model 330. In this embodiment, the server computing environment 320 has preselected the feedback data context model 330 accessed via the link 620A. After the server computing environment 320 receives the request 315, the server computing environment 320 transmits the interface for the feedback data context model 330 to the client computing environment 315. In the exemplary embodiment of the access screen 610A illustrated in FIG. 6A, the access screen 610A is provided within an email message.

FIG. 6B illustrates a second embodiment of an access screen 610B which comprises a link 620B for accessing an interface of a feedback data context model 330. The link 620B is personalized for the user of the smart phone 600. When the user selects the link 620B, the smart phone 600 sends a request 315 to the server computing environment 320 to gain access to the interface of the linked-to feedback data context model 330. In this embodiment, the server computing environment 320 has preselected the feedback data context model 330 accessed via the link 620B. After the server computing environment 320 receives the request 315, the server computing environment 320 transmits the interface for the feedback data context model 330 to the client computing environment 315. In the exemplary embodiment of the access screen 610B illustrated in FIG. 6B, the access screen 610B is provided within a Short Message Service (SMS) message, i.e., a text message.

In the exemplary embodiment illustrated in FIG. 6A noted above, the access screen 610 is an email message which has been delivered to the smart phone 600, i.e., the access screen 610A has been "pushed" to the smart phone 600. In the exemplary embodiment illustrated in FIG. 6B noted above, the access screen 610B is an SMS message which has also been pushed to the smart phone 600. Other ways of pushing the access screen 610A, 610B to the user are contemplated, and it is to be understood that the examples given herein are not limiting. For example, other means for pushing the access screen 610A, 610B include a Facebook message, a web chat session, etc.

Other exemplary embodiments in which an access screen is "pulled" are contemplated. For example, in another exemplary embodiment, using a web browser of the smart phone 600, the user may navigate the browser to a web page to an access screen, from which the interface of the feedback data context model 330 is accessed. For example, the user may type a URL address into the browser of the smart phone to navigate to the access screen. Alternatively, the user may capture a QR code that is encoded with an URL to navigate to the access screen.

FIGS. 6C through 6G illustrate exemplary screenshots of the interface for the feedback data context model 330, which interface is provided to the smart phone 600, which is a client computing environment, by the server computing environment 320 via the application 180, in accordance with an exemplary embodiment of the present invention. In the exemplary embodiment illustrated in FIGS. 6C through 6G, the interface is provided in a web application that is accessed via a webpage that runs on the smart phone 600. The webpage is communicated by the server computer environment 320 to the smart phone 600 and rendered in a web browser running on the smart phone 600. It is to be understood that the interface is not so limited. Other exemplary embodiments in which the interface is provided in an app 180 which the smart phone 600A downloads from the server computing system(s) 220 and which does not require a browser to run are contemplated.

Figure 6D:
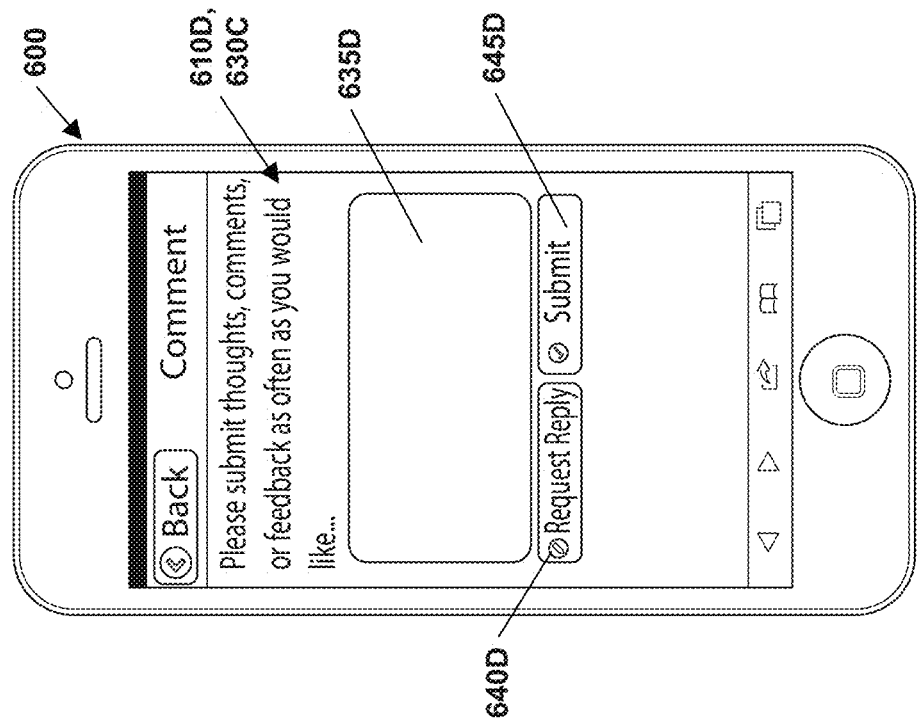
Figure 6C:
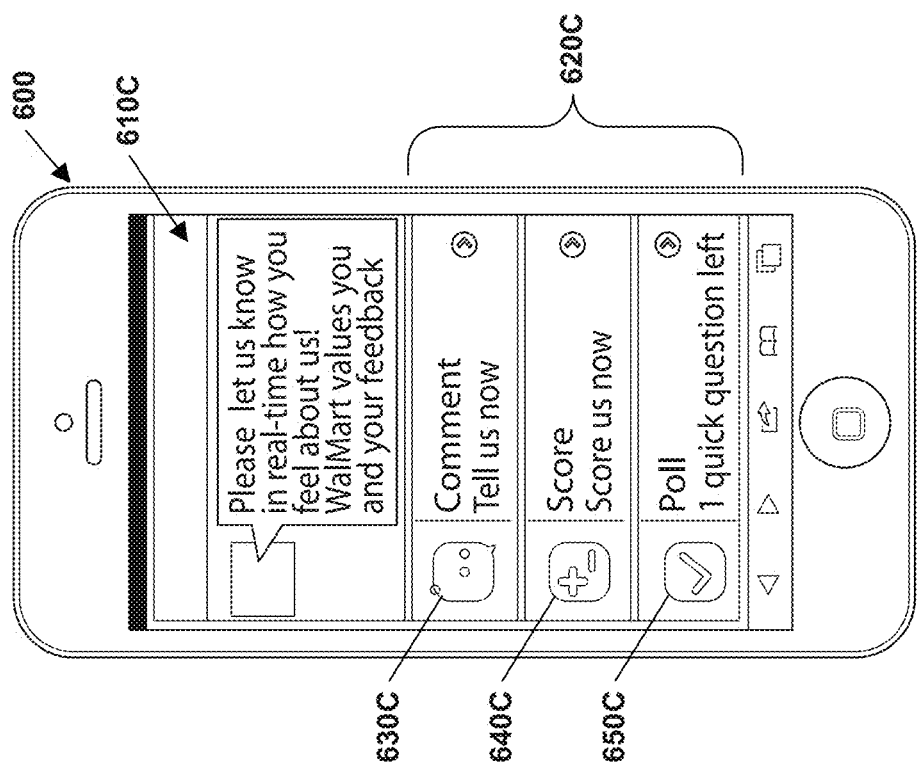

FIG. 6C illustrates a screenshot of a main screen 610C of the interface provided to the client computing environment 315 as a result of the user selecting the link 620A, 620B. The main screen 610C provides a portal 620C to various portions of the interface, namely a "Comment" section 630C, a "Score" section 640C, and a "Poll" section 650C.

FIG. 6D illustrates a screen 610D in the Comment section 630D, which comprises a text field 635D for inputting comments, a button 640D which the user may select to request that the entity for which feedback is being left provide a reply, and a button 645D to submit the comments inputted into the text field 635D to the server computing environment 320 as the data 315.

Figure 6F:
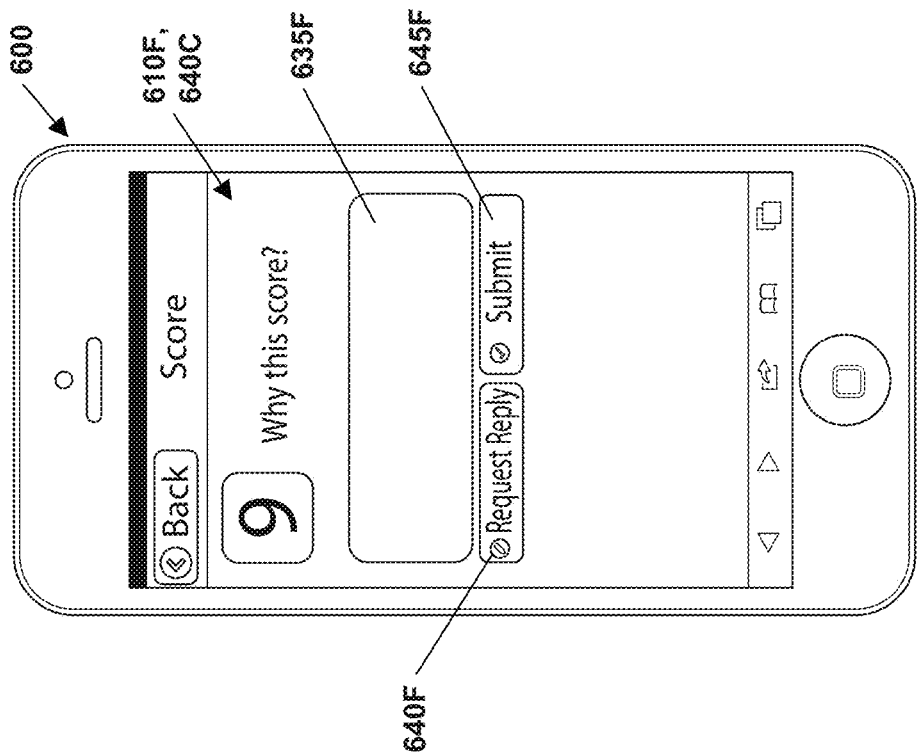
Figure 6E:
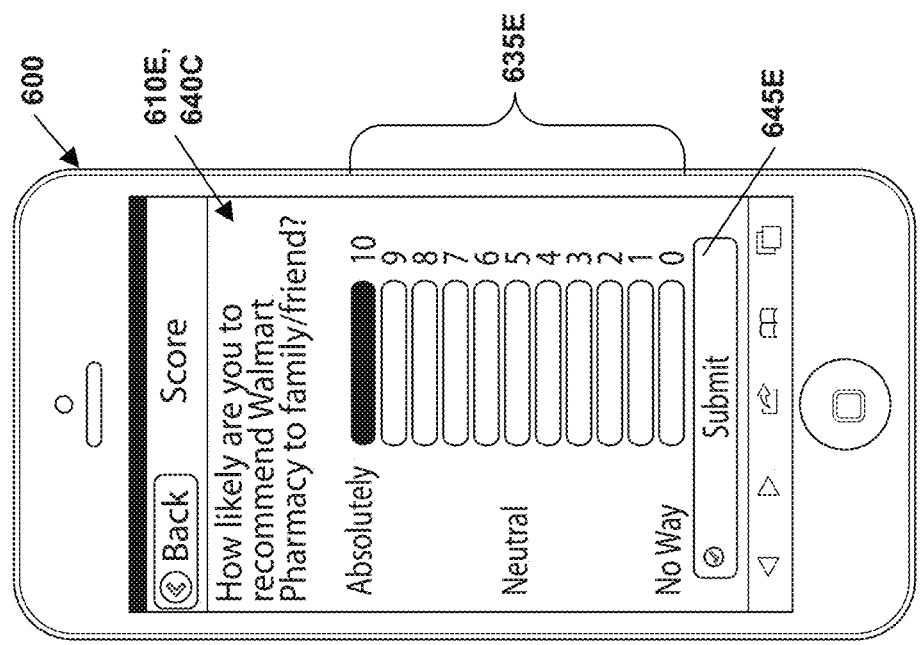

FIG. 6E illustrates a first screen 610E in the Score section 640C, the first screen 610E comprising a plurality of ratings 635E, from which the user may select one as feedback for a product or service received. After selecting one of the ratings 635E, the user commands the smart phone to transmit the polling response to the server computing environment 320 as the data 315 by selecting a submit button 645E.

FIG. 6F illustrates a second screen 610F in the Score section 640C, the second screen 610F comprising a text field 635F for inputting comments regarding the answered Score, a button 640F which the user may select to make the text field 635F editable, and a button 645F to submit the comments inputted into the text field 635F to the server computing environment 320 as the data 315.

Figure 6G:
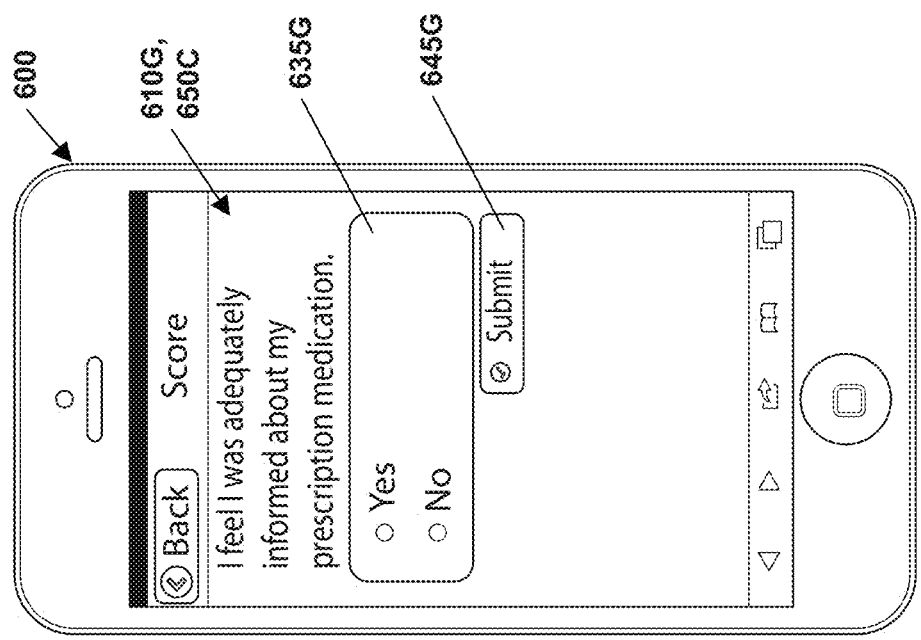

FIG. 6G illustrates a screen 610G in the Poll section 650C, which comprises an input field 635G for inputting a response to a poll question and a button 645G to submit the inputted response to the server computing environment 320 as the data 315. The poll questions are specified by the context model established in the method 500.

Figure 7A:
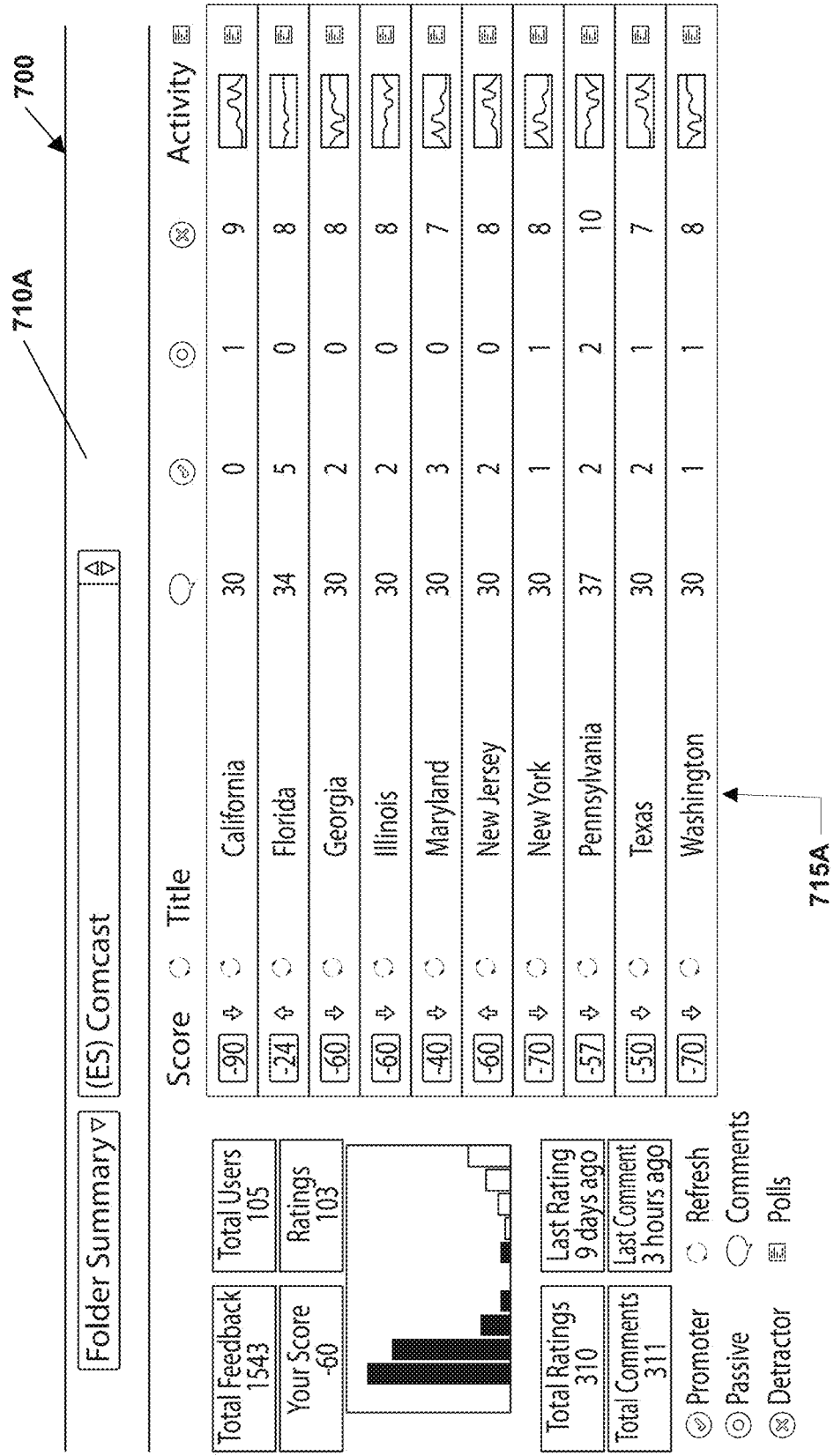
FIGS. 7A-7C illustrate screenshots of a dashboard for viewing feedback data provided by users, in accordance with an exemplary embodiment of the present invention.
Figure 7B:
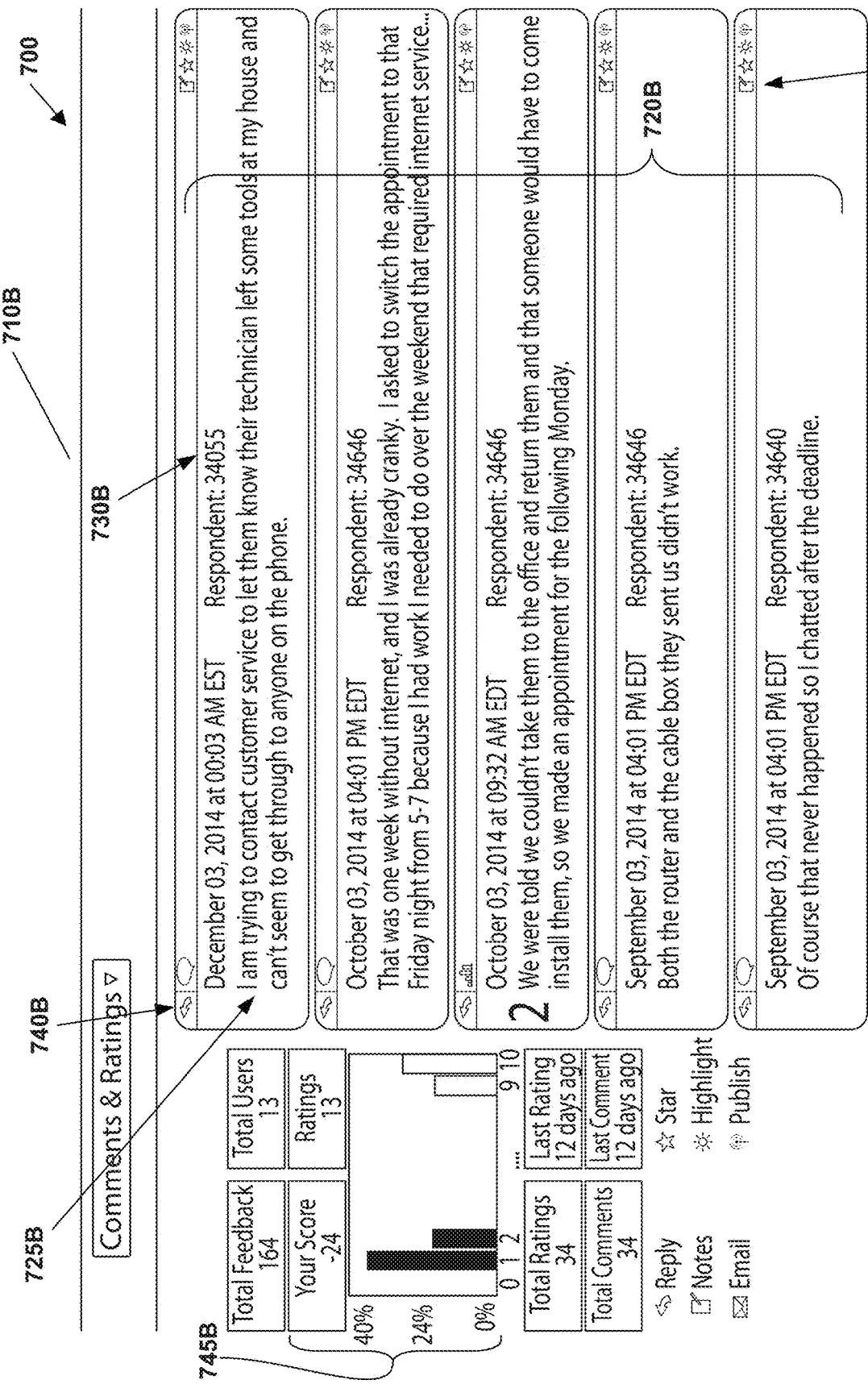
Figure 7C:

Referring now to FIGS. 7A through 7C, there are illustrated exemplary screenshots of a dashboard 700, in accordance with an exemplary embodiment of the present invention. As described below, the dashboard 700 is provided with data or updated with data, as specified by the Step 435. FIG. 7A illustrates a main screen 710A, which provides a link 715A to feedback left for service or products.

FIG. 7B illustrates a screen 710B that collects all Comment and Scoring feedback regarding a specific service or product selected via a link 715A in the main screen 710A. The screen 710B comprises a plurality of entries 720B, each of which includes a comment 725B and associated metadata, e.g., the location from which the comment 725B was made, the stage of service being received by the user, information relating to the user derived from another source (as discussed below with regard to FIG. 8), e.g., from an electronic medical record (e.g., drug therapies, clinical data, physician data), weather data, or any electronic record/data associated with the customer, etc., a customer ID 730B, a link 735B by which the user accessing the dashboard 700 may comment on a comment 720B, and a link 740B to respond to the comment, if the commenter requested a reply by clicking the button 640D. The server computing environment 320 tallies the ratings received for the service or product, averages them, and reports them in a panel 745B.

FIG. 7C illustrates a screen 710C summarizing the results of Polling feedback for a service or product, in accordance with an exemplary embodiment of the present invention.

It is to be understood that the dashboard 700 can comprise data representative of processed real time aggregated feedback data (e.g., a combination of feedback data from any number, n, of feedback data context models 330) received from a number of participating users (not shown) according a selected feedback data context model 330 (e.g., healthcare services) according to a selected feedback data analytic methodology (e.g., net promoter scoring methodology). The exemplary dashboard 700, as shown, can comprise data representative of alternate feedback data that can be operably received by exemplary context based feedback environment 300. In the illustrative implementation, the dashboard can comprise character limited text feedback data illustrative of descriptive comments from various participating users that are elicited according a selected feedback data context model (e.g., users providing a text description of being checked in for an in-patient procedure at a hospital, the user being prompted in real-time during or within a selected short period of time after check-in). Feedback may further comprise audio-visual data, such as images, video, audio clips, etc.

Figure 8:
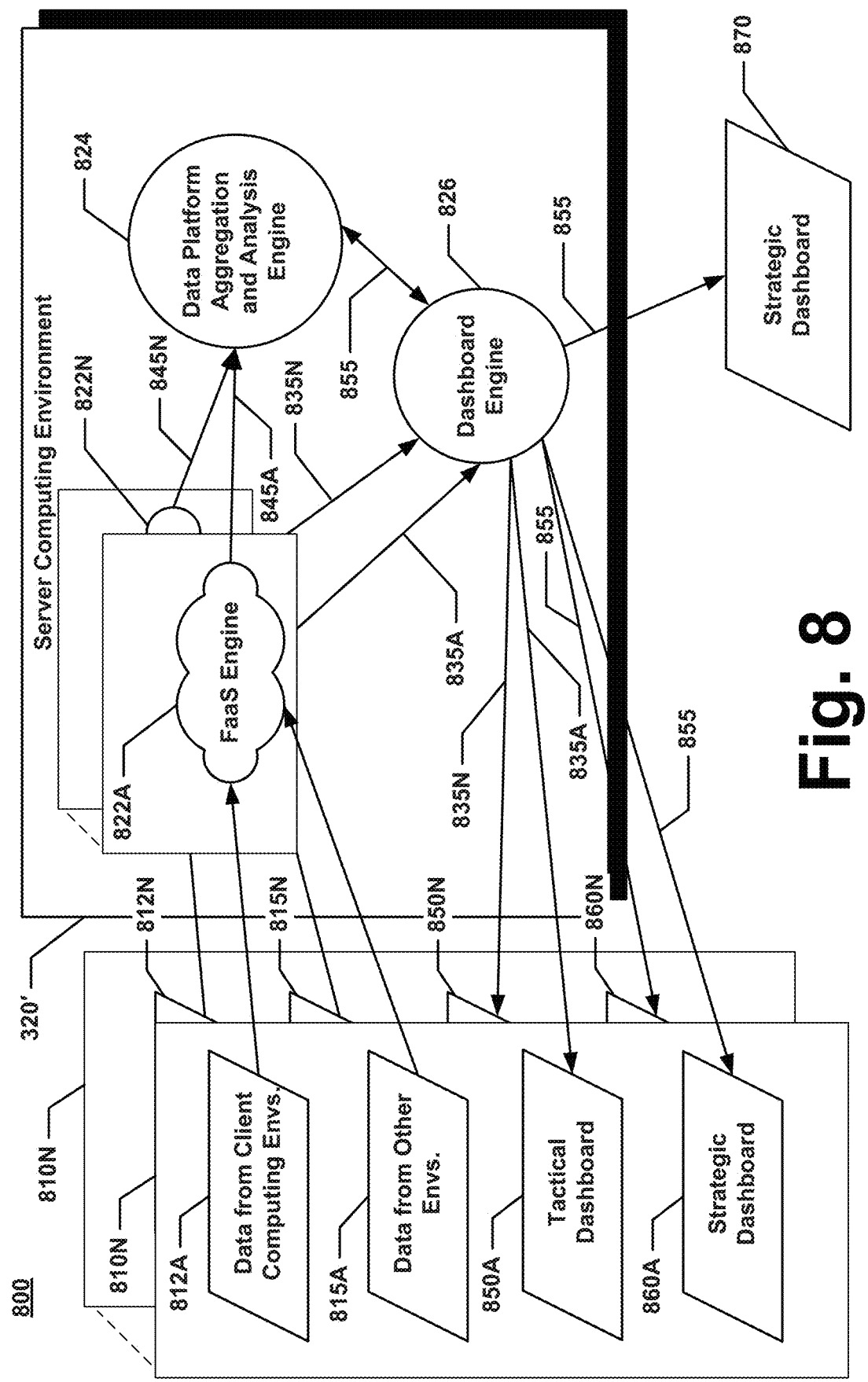
FIG. 8 illustrates an exemplary alternative embodiment of the context-based feedback data computing environment of FIG. 3, in accordance with an exemplary embodiment of the present invention.

Referring now to FIG. 8, there is illustrated an exemplary alternative embodiment of the feedback data environment 300, which exemplary alternative embodiment is generally designated as 800, in accordance with an exemplary embodiment of the present invention. FIG. 8 illustrates select portions of the feedback data environment 800, specifically those portions of the feedback data environment 800 which differ from the feedback data environment 300. The differences are discussed below.

The feedback data environment 800 comprises an exemplary alternative embodiment of the server computing environment 320, generally designated in FIG. 8 as server computing environment 320'. The server computing environment 320' comprises a plurality of Feedback-as-a-Service (FaaS®) engines 822A through 822N, one for each entity that has engaged the provider of the server computing environment 320 to track feedback from customers of the entity. The server computing environment 320' further comprises a data platform aggregation and analysis engine 824, and a dashboard engine 826. FIG. 8 illustrates that N entities (810A through 810N) have engaged the provider of the server computing environment 320 to track feedback from customers of each entity 810A through 810N.

The server computing environment 320', or more specifically each FaaS engine 822A through 822N, receives the data from the customers of its respective entity 810A through 810N in the Step 420. For each entity 810A through 810N, such data comprises respective data from client computing environments 812A through 812N and respective data from other environments 815A through 815N. Such other environments are contemplated as being independently existing data sources, i.e., data sources that exist independently from the feedback data environment 800. As such, the data 815A through 815N may be sourced from Hospital Consumer Assessment of Health Providers and System (HCAPHS) surveys, and other existing quality metrics data, electronic medical records (EMRs), electronic health records (EHRs), data from practice management software (PMS), sensor data (from wearable or remote sensors and embedded medical devices), and location and other meta data, including social media feeds.

The FaaS engines 822A through 822N provide the portion of the data 812A through 812N and 815A through 815N that is tied to a user, e.g., a patient, to the dashboard engine 826 as data 835A through 835N, respectively, in the Step 430. The dashboard engine 426 provides the data 835A through 835N to tactical dashboards 850A through 850N, respectively, in the Step 435. The tactical dashboards 850A through 850N are respectively accessible by the entities 810A through 810N. The dashboard engine 826 configures the tactical dashboards 850A through 850N to include views previously configured by administrators of the tactical dashboards 850A through 850N. Any of the entities 810A through 810N may implement one or more workflows, e.g., corrective actions, based on the data 835A through 835N in response to the feedback provided in the respective data 812A through 812N. For example, if the entity 810A is a hospital and the data 812A, 835A indicates that a patient is unhappy with the level of noise, the entity 810A may take corrective action to reduce the noise level in the hospital.

In the exemplary embodiment described above, the tactical dashboards 850A through 850N comprise personal data of the users that provided the feedback so that their respective entities 810A through 810N that provided products or services consumed by the users are able to specifically identify such user's experiences. For clarity, the entities 810A through 810N have access only to their respective tactical dashboards 850A through 850N, and the dashboard 850A through 850N contain the personal information of only the respective data 812A through 812N and the respective data 815A through 815N. One entity cannot gain access to personal information of users associated with another entity.

The FaaS engines 822A through 822B provide the data 812A through 812N and 815A through 815N to a service that strips out personal information from the data, i.e., information that identifies users, e.g., patients, to provide anonymous data and forwards such data as data 845A through 845N to the data platform aggregation and analysis engine 824 in the Step 430. The data platform aggregation and analysis engine 824 performs one or more algorithms to process the data 845 through 845N. Such algorithms include pattern recognition, feature detection, clustering, subset selection, and semantic analysis. The data platform aggregation and analysis engine 824 provides resulting data 855 to the dashboard engine 826 in the Step 430, and the dashboard engine 826 provides the data 855 to strategic dashboards 860A through 860N in the Step 435. The strategic dashboards 860A through 860N are respectively associated with the entities 810A through 810N. The strategic dashboards 860A through 860N allow the administrator of their respective entities 810A through 810N to view experiential telemetry, industry trends, rankings, and comparisons, set benchmarks, and identify best practices based on the aggregated, de-personalized data 855.

In an exemplary embodiment, the dashboard engine 826 also provides the data 855 to a further strategic dashboard 870. The strategic dashboard 870 is accessible by an entity that is not associated with customers providing feedback. Such entity may still arrange to have access to the strategic dashboard 870 for research purposes, industry surveys, market research, etc.

In an exemplary embodiment, the server computing environment 320, 320' allows a feedback administrator to track a user as he or she consumes a good or service at various stages. Because the access screen 610A, 610B may be pushed to a user's smart phone 600, the user's identity may be reasonably inferred and linked to his or her phone number. The user may also be associated with a global unique identifier (GUID). Thus, all feedback that a user may provide may be linked in the server computing environment 320, 320' by the GUID of the user so that the user's experience may be tracked over time. Such feedback and the GUID of the user may be stored by the server computing environment 320, 320' in the data store 122.

It is understood that the herein described systems and methods are susceptible to various modifications and alternative constructions. There is no intention to limit the herein described systems and methods to the specific constructions described herein. On the contrary, the herein described systems and methods are intended to cover all modifications, alternative constructions, and equivalents falling within the scope and spirit of the herein described systems and methods.

It should also be noted that the herein described systems and methods can be implemented in a variety of electronic environments (including both non-wireless and wireless computer environments, including cell phones and video phones), partial computing environments, and real world environments. The various techniques described herein may be implemented in hardware or software, or a combination of both. Preferably, the techniques are implemented in computing environments maintaining programmable computers that include a computer network, processor, servers, a storage medium readable by the processor (including volatile and non-volatile memory and/or storage elements), at least one input device, and at least one output device. Computing hardware logic cooperating with various instructions sets are applied to data to perform the functions described above and to generate output information. The output information is applied to one or more output devices. Programs used by the exemplary computing hardware may be preferably implemented in various programming languages, including high level procedural or object oriented programming language to communicate with a computer system. Illustratively the herein described apparatus and methods may be implemented in assembly or machine language, if desired. In any case, the language may be a compiled or interpreted language. Each such computer program, application, Java Script, applet, or other executable code is preferably stored on a storage medium or device (e.g., ROM or magnetic disk) that is readable by a general or special purpose programmable computer for configuring and operating the computer when the storage medium or device is read by the computer to perform the procedures described above. The apparatus may also be considered to be implemented as a computer-readable storage medium, configured with a computer program, where the storage medium so configured causes a computer to operate in a specific and predefined manner.

Although exemplary implementations of the herein described systems and methods have been described in detail above, those skilled in the art will readily appreciate that many additional modifications are possible in the exemplary embodiments without materially departing from the novel teachings and advantages of the herein described systems and methods. Accordingly, these and all such modifications are intended to be included within the scope of the herein described systems and methods. The herein described systems and methods may be better defined by the following exemplary claims.

What is claimed is:

1. A context-based feedback system comprising:
a computing processor; and
a computing memory communicatively coupled with the computing processor, the computing memory having stored therein instructions that, when executed by the computing processor, cause the computing processor to perform steps of:
retrieving data representative of a context model based upon at least one criterion that triggers at least one request for input of feedback data;
transmitting the at least one request to each client computer, where one client computer is provided for each system entity user that has engaged a provider of the context-based feedback system;
receiving feedback data of entity customers of one or more system entity users, from the respective client computer of the system entity user, in response to the at least one request;
processing the feedback data, which in a first aspect, comprises the steps of:
removing personal, entity customer identifying, information from the feedback data to create anonymous feedback data;
applying one or more algorithms to the anonymous feedback data to create anonymous resulting data;
forwarding the anonymous resulting data to a strategic dashboard of the respective client computer of the system entity user, where each strategic dashboard of the respective client computer of the system entity user includes identical anonymous resulting data, where each strategic dashboard is configured to retain the anonymous resulting data originating from the feedback data of each entity customer of each system entity user, where each strategic dashboard allows only the system entity user associated with the respective strategic dashboard access to the anonymous resulting data contained thereon, whereby the system entity user associated with the respective strategic dashboard can perform research, industry surveys, or market investigation using the anonymous resulting data;
processing the feedback data, which in a second aspect, comprises the steps of:
evaluating the feedback data based upon origination of the feedback data from the entity customers of the one or more system entity users to create compiled data lists, where the feedback data is separated into the compiled data lists based upon feedback data association with each system entity user, where feedback data of all entity customers of a respective system entity user are grouped together, and where a compiled data list of each system entity user includes personal, identifying information of respective entity customers of the respective system entity user; and
forwarding the compiled data list of each system entity user to a tactical dashboard of the respective client computer of the system entity user, where each tactical dashboard allows only the system entity user associated with the respective tactical dashboard access to the compiled data list of each system entity user, whereby the system entity user associated with the respective tactical dashboard can perform research, industry surveys, or market investigation using the compiled data list of each system entity user, with access to the personal, identifying information of their entity customers; and
wherein one system entity user cannot access personal, identifying information of any entity customer of another system entity user.

2. The system of claim 1, wherein the at least one criterion includes one or more timelines or conditions, associated with a good or service acquired by the entity customers from their respective system entity user, that trigger the at least one request for input of feedback data and that determines to which client computer the at least one request is transmitted.

3. The system of claim 1, wherein the instructions, when executed by the computing processor, cause the computing processor to perform a further step of:
prior to the operation of retrieving, transmitting a link to the respective client computer of the system entity user, wherein the link is configured to cause the respective client computer of the system entity user to send a request to the computing processor to perform the operation of retrieving, wherein the link is personalized for an entity customer of the respective system entity user associated with the respective client computer of the system entity user, the link being associated with a preselected context model for each entity customer of the respective system entity user, the preselection of the context model and the personalization of the link being based upon one or more timelines or conditions associated with a good or service acquired by the entity customer of the respective system entity user.

4. The system of claim 3, wherein the step of transmitting the link to the respective client computer of the system entity user is performed in response to a request by the respective client computer of the system entity user.

5. The system of claim 1, wherein the one or more algorithms comprise any one of pattern recognition, feature detection, subset selection, or semantic analysis.

6. A context-based feedback method comprising steps of:
retrieving, from a data store, data representative of a context model based upon at least one criterion that triggers one or more requests for input of feedback data;
wherein the at least one criterion includes one or more timelines or conditions, associated with a good or service acquired by entity customers from one or more system entity users, that trigger the one or more requests and that determine to which client computer or client computers the one or more requests are transmitted, where one client computer is provided for each system entity user;
transmitting, by a computing processor, each request to the a respective client computer of each system entity user associated with a respective entity customer, over a computer network;
receiving, by the computing processor, feedback data of the entity customers of the one or more system entity users, from each respective client computer of each system entity user associated with the respective entity customer, in response to the one or more requests;
receiving, by the computing processor, independent data of each entity customer providing feedback data, where the independent data is independent of the feedback data received, and includes personal, entity customer identifying information;
processing, by the computing processor, the feedback data and the independent data, where in a first aspect, the processing comprises the steps of:
removing personal, entity customer identifying, information from the feedback data and the independent data to create anonymous feedback data;

applying one or more algorithms to the anonymous feedback data to create anonymous resulting data;

forwarding the anonymous resulting data to a strategic dashboard of each respective client computer of the system entity user associated with the respective entity customer, where each strategic dashboard of each respective client computer includes identical anonymous resulting data, where each strategic dashboard is configured to retain the anonymous resulting data originating from the feedback data and the independent data of each entity customer of each system entity user, wherein each strategic dashboard allows only the system entity user associated with the respective strategic dashboard access to the anonymous resulting data contained thereon, whereby the system entity user associated with the respective strategic dashboard can perform research, industry surveys, or market investigation using the anonymous resulting data;

processing, by the computing processor, the feedback data and the independent data, where in a second aspect, the processing comprises the steps of:

evaluating the feedback data and the independent data based upon origination of the feedback data and the independent data from the entity customers of the one or more system entity users to create compiled data lists, where the feedback data and the independent data is separated into the compiled data lists based upon feedback data and independent data association with each system entity user, where feedback data and independent data of all entity customers of a respective system entity user are grouped together, and where a compiled data list of each system entity user includes personal, identifying information of respective entity customers of the respective system entity user; and forwarding the compiled data list of each system entity user to a tactical dashboard of the respective client computer of the system entity user, where each tactical dashboard allows only the system entity user associated with the respective tactical dashboard access to the compiled data list of each system entity user, whereby the system entity user associated with the respective tactical dashboard can perform research, industry surveys, or market investigation using the compiled data list, with access to the personal, identifying information of their entity customers; and wherein one system entity user cannot access personal, identifying information of any entity customer of a not her system entity user.

7. The method of claim 6, further comprising a step of:
prior to the operation of retrieving, transmitting a link to the respective client computer of the system entity user associated with the respective entity customer, wherein the link is configured to cause the respective client computer to send a request to the computing processor to perform the operation of retrieving, wherein the link is personalized for an entity customer of the respective system entity user associated with the respective client computer, the link being associated with a preselected context model for each entity customer, the preselection of the context model and the personalization of the link being based upon one or more timelines or conditions associated with a good or service acquired by each entity customer from their respective system entity user.

8. The method of claim 6, wherein the one or more algorithms comprise any one of pattern recognition, feature detection, subset selection, or semantic analysis.

9. A context-based feedback system comprising:
multiple computing processors, including one or more feedback-as-a-service engines, a data platform aggregation and analysis engine, and a dashboard engine, wherein one feedback-as-a-service engine is associated with each system entity user of the context-based feedback system requesting feedback from entity customers of each system entity user; and a computing memory communicatively coupled with each computing processor, the computing memory having stored therein instructions that, when executed by a respective computing processor, causes the respective computing processor to perform steps of:

retrieving data representative of a context model comprising at least one criterion that triggers one or more requests for input of feedback data;

wherein the at least one criterion includes one or more timelines or conditions that trigger the one or more requests, and that determine to which client computer or client computers the one or more requests are transmitted to reach the respective entity customer, where one client computer is provided for each system entity user, and each system entity user is associated with one or more entity customers;

transmitting the at least one request to the respective client computer or client computers;

receiving feedback data from the respective client computer or client computers, from the respective entity customer, in response to the one or more requests, wherein the feedback data from the respective entity customer is received only by the feedback-as-a-service engine of the system entity user associated with the respective entity customer;

receiving independent data from the respective client computer or client computers, for the respective entity customer, based upon the one or more requests, where the independent data is independent of the feedback data received, for the respective entity customer, and includes personal, customer identifying information of the respective entity customer, and where the independent data of the respective entity customer is received only by the feedback-as-a-service engine of the system entity user associated with the respective entity customer;

processing the feedback data and the independent data, where in a first aspect, the processing comprises the steps of:

removing personal, entity customer identifying, information from the feedback data and the independent data to create anonymous feedback data;

applying one or more algorithms to the anonymous feedback data to create anonymous resulting data;

forwarding the anonymous resulting data to a strategic dashboard of each client computer or client computers, where each strategic dashboard of each client computer or client computers includes identical anonymous resulting data, where each strategic dashboard is configured to retain the anonymous resulting data originating from the feedback data and the independent data of the respective entity customer of each system entity user, where each strategic dashboard allows only the system entity user associated with the respective strategic dashboard access to the anonymous resulting data contained thereon, whereby the system entity user associated with the respective strategic dashboard can perform research, industry surveys, or market investigation using the anonymous resulting data; and processing the feedback data, which in a second aspect, comprises the steps of:

evaluating the feedback data based upon origination of the feedback data from the entity customers of the one or more system entity users to create compiled data lists, where the feedback data is separated into the compiled data lists based upon feedback data association with each system entity user, where feedback data of all entity customers of a respective system entity user are grouped together, and where the compiled data list of each system entity user includes personal, identifying information of respective entity customers of the respective system entity user; and forwarding the compiled data list of each system entity user to a tactical dashboard of the respective client computer of the system entity user, where each tactical dashboard allows only the system entity user associated with the respective tactical dashboard access to the compiled data list of each system entity user, whereby the system entity user associated with the respective tactical dashboard can perform research, industry surveys, or market investigation using the compiled data list of each system entity, with access to the personal, identifying information of their entity customers;

wherein one system entity user cannot access personal, identifying information of any entity customer of another system entity user.

10. The system of claim 9, where each strategic dashboard allows an administrator of the respective system entity user to selectively view experiential telemetry, industry trends, rankings, and comparisons, to set benchmarks, and to identify best practices based on the anonymous resulting data.

11. The system of claim 9, wherein the independent data is sourced from one or more of Hospital Consumer Assessment of Health Providers and System (HCAPHS) surveys, electronic medical records (EMRs), electronic health records (EHRs), data from practice management software (PMS), sensor data (from wearable or remote sensors and embedded medical devices), and location and other meta data, including social media feeds.

* * * * *